United States Patent
Zhang

(10) Patent No.: US 12,383,327 B2
(45) Date of Patent: Aug. 12, 2025

(54) MULTI-CHANNEL RF IMPEDANCE

(71) Applicants: SMITH & NEPHEW, INC., Memphis, TN (US); SMITH & NEPHEW ORTHOPAEDICS AG, Zug (CH)

(72) Inventor: Hongxuan Zhang, Austin, TX (US)

(73) Assignees: SMITH & NEPHEW, INC., Memphis, TN (US); SMITH & NEPHEW ORTHOPAEDICS AG, Zug (CH)

(*) Notice: Subject to any disclaimer, the term of this patent is extended or adjusted under 35 U.S.C. 154(b) by 340 days.

(21) Appl. No.: 17/460,631

(22) Filed: Aug. 30, 2021

(65) Prior Publication Data

US 2022/0071685 A1    Mar. 10, 2022

Related U.S. Application Data

(60) Provisional application No. 63/074,673, filed on Sep. 4, 2020.

(51) Int. Cl.
  *A61B 18/12* (2006.01)
  *A61B 18/14* (2006.01)
  *A61B 18/00* (2006.01)

(52) U.S. Cl.
  CPC .......... *A61B 18/1206* (2013.01); *A61B 18/14* (2013.01); *A61B 2018/00577* (2013.01); *A61B 2018/00589* (2013.01); *A61B 2018/00732* (2013.01); *A61B 2018/00755* (2013.01); *A61B 2018/128* (2013.01)

(58) Field of Classification Search
  CPC ................ A61B 18/1206; A61B 18/14; A61B 2018/00577; A61B 2018/00589; A61B 2018/00732; A61B 2018/00755; A61B 2018/128; A61B 18/148; A61B 2018/00642; A61B 2018/00875; A61B 2018/1472; A61B 2218/002; A61B 2218/007
  See application file for complete search history.

(56) References Cited

U.S. PATENT DOCUMENTS

| | | | |
|---|---|---|---|
| 3,245,408 A | 4/1966 | Gonser | |
| 6,632,193 B1* | 10/2003 | Davison | A61B 18/1402 606/41 |
| 7,204,835 B2 | 4/2007 | Latterell et al. | |

(Continued)

FOREIGN PATENT DOCUMENTS

| | | | | |
|---|---|---|---|---|
| AU | 2009225304 A1 * | 4/2010 | ......... | A61B 18/1445 |
| AU | 2014201216 A1 * | 10/2014 | ......... | A61B 18/1206 |

(Continued)

*Primary Examiner* — Joanne M Rodden
*Assistant Examiner* — Dana Stumpfoll
(74) *Attorney, Agent, or Firm* — Dickinson Wright PLLC

(57) ABSTRACT

Electrosurgical systems and methods. At least one example embodiment is a method including: performing a first electrosurgical activity by way of first energy at a first frequency applied to an active electrode of an electrosurgical wand, the application of the first energy by way of an electrosurgical generator, and the first electrosurgical activity produces a first effect that is tissue-altering; and measuring an electrosurgical parameter by way of a second energy at a second frequency applied to the active electrode, the measuring simultaneously with the performing of the first electrosurgical activity, and the second frequency different than the first frequency.

20 Claims, 8 Drawing Sheets

(56) References Cited

U.S. PATENT DOCUMENTS

| | | | |
|---|---|---|---|
| 8,430,874 B2* | 4/2013 | Newton | A61B 18/1206 |
| | | | 607/101 |
| 9,522,036 B2* | 12/2016 | Panescu | A61B 5/6852 |
| 10,188,448 B2 | 1/2019 | Friedrichs | |
| 2002/0022836 A1 | 2/2002 | Goble et al. | |
| 2008/0281316 A1* | 11/2008 | Carlton | A61B 18/1445 |
| | | | 606/34 |
| 2013/0123778 A1* | 5/2013 | Richardson | A61B 18/1492 |
| | | | 606/41 |
| 2014/0025065 A1 | 1/2014 | Marion | |
| 2014/0214028 A1* | 7/2014 | Gelbart | A61B 5/4875 |
| | | | 606/41 |

FOREIGN PATENT DOCUMENTS

| | | | | |
|---|---|---|---|---|
| WO | 200219932 A1 | 3/2002 | | |
| WO | WO-2022046443 A1 * | 3/2022 | | A61B 18/1492 |

* cited by examiner

MULTI-CHANNEL RF IMPEDANCE

CROSS-REFERENCE TO RELATED APPLICATIONS

This application claims the benefit of U.S. Provisional App. No. 63/074,673 filed Sep. 4, 2020 titled "Electrosurgical Systems and Methods." The provisional application is incorporated by reference herein as if reproduced in full below.

BACKGROUND

Electrosurgical systems are used by surgeons to perform specific functions during surgical procedures. Within these procedures, the surgeons may treat more than one type of tissue or create more than one tissue effect (e.g., ablation and coagulation). Switching between tissue effects in the related art (e.g., switching between ablation and coagulation) may take place based on the surgeon's visual inspection of the surgical site. For example, if excess blood is noted during ablation, the surgeon may switch to a coagulation mode for a period time, and then switch back to ablation. However, in some cases, by the point in time at which the visual inspection shows bleeding, excessive bleeding may have already taken place. Moreover, manually switching back and forth between the example ablation mode and coagulation mode may extend the duration of the surgical procedure.

Any system or method that decreases surgical time, and produces better patient outcomes, would provide a competitive advantage in the marketplace.

BRIEF DESCRIPTION OF THE DRAWINGS

For a detailed description of example embodiments, reference will now be made to the accompanying drawings in which.

DEFINITIONS

Figure 1:
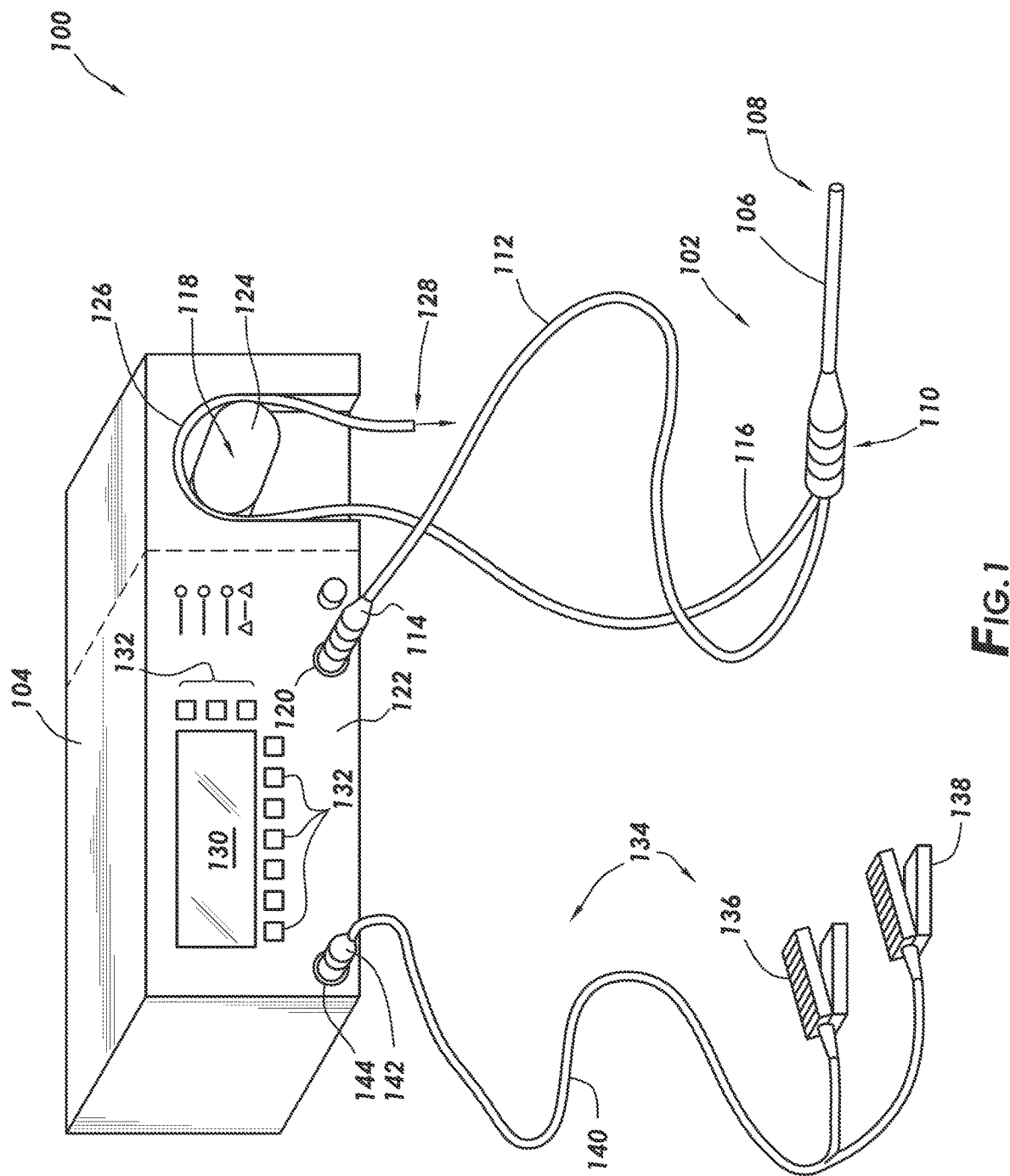
FIG. 1 shows an electrosurgical system in accordance with at least some embodiments.

Various terms are used to refer to particular system components. Different companies may refer to a component by different names—this document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

"Electric motor" shall include alternating current (AC) motors, direct current (DC) motors, as well as stepper motors.

In relation to electrical devices, the terms "input" and "output" refer to electrical connections to the electrical devices, and shall not be read as verbs requiring action. For example, a differential amplifier (such as an operational amplifier) may have a first differential input and a second differential input, and these "inputs" define electrical connections to the operational amplifier, and shall not be read to require inputting signals to the operational amplifier.

"Processor" shall mean, alone or in combination, individual circuit components, an application specific integrated circuit (ASIC), a microcontroller with controlling software, a digital signal processor (DSP), a processing core (reduced instruction set core (RISC)) with controlling software, or a field programmable gate array (FPGA), configured to read inputs and drive outputs responsive to the input.

Where a range of values is provided, it is understood that every intervening value, between the upper and lower limit of that range and any other stated or intervening value in that stated range is encompassed within the disclosure. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to electrosurgical systems and methods. In particular, various examples are directed to electrosurgical methods that may include performing an electrosurgical activity (e.g., ablation, coagulation) with energy at a first frequency, and simultaneously measuring an electrosurgical parameter by way of energy at a second frequency, where the second frequency is different than the first frequency. More particularly still, various example embodiments are based on a discovery that various tissue, bone, and/or fluids (e.g., blood, saline) may each have a characteristic frequency better suited for detection of presence and/or proximity to active electrode. Better control of an electrosurgical procedure may be implemented by measuring electrosurgical parameters at frequencies different than frequencies at which energy creates tissue altering effects. The specification first turns to an example system to orient the reader.

FIG. 1 shows an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle 110 on a proximal end, where a surgeon grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 is coupled to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used in some cases to provide aspiration at the distal end 108 of the wand. In accordance with various embodiments, the flexible tubular member 116 is coupled to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in the figure), but in any event the peristaltic pump may be operatively coupled to the controller 104. In yet still other cases, the peristaltic pump 118 may be omitted.

The example peristaltic pump 118 comprises a rotor portion 124 (hereafter just "rotor 124") as well as a stator portion 126 (hereafter just "stator 126"). The flexible tubular member 116 is coupled within the peristaltic pump 118 between the rotor 124 and the stator 126, and movement of the rotor 124 against the flexible tubular member 116 causes fluid movement toward the discharge 128. While the example peristaltic pump 118 is shown with the rotor 124 having two heads, varying types of peristaltic pumps 118 may be used (e.g., a five head peristaltic pump). In example embodiments, the peristaltic pump 118 creates a volume-controlled aspiration from a surgical field at the distal end 108 of the wand 102, with the control based on a speed of the rotor 124, as commanded by the controller 104. Alternately, the peristaltic pump 118 may control fluid flow to the surgical site through the wand 102.

Still referring to FIG. 1, a display device or interface device 130 is visible through the enclosure 122 of the controller 104, and in some embodiments a user may select operational modes of the controller 104 by way of the interface device 130 and/or related buttons 132. For example, using one or more of the buttons 132 the surgeon may select among various ablation modes, or switch between ablation and coagulation.

In some embodiments the electrosurgical system 100 also comprises a foot pedal assembly 134. The foot pedal assembly 134 may comprise one or more pedal devices 136 and 138, a flexible multi-conductor cable 140, and a pedal connector 142. While only two pedal devices 136 and 138 are shown, one or more pedal devices may be implemented. The enclosure 122 of the controller 104 may comprise a corresponding connector 144 that is coupled to the pedal connector 142. A surgeon may use the foot pedal assembly 134 to control various aspects of the controller 104, such as the mode of ablation, or switching between ablation and coagulation. In other embodiments, control of the various operational or performance aspects of controller 104 may be activated by selectively depressing finger buttons located on handle 110 of wand 102 (the finger buttons not specifically shown).

The electrosurgical system 100 of the various embodiments may employ Coblation® technology. In particular, the assignees of the present disclosure are the owners of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments, such as surgical procedures involving a knee or shoulder, the electrically conductive fluid may be delivered in the vicinity of the active electrode and/or to the target site by a delivery system separate and apart from the electrosurgical system 100.

When the electrically conductive fluid is energized to the point that the atoms of the fluid vaporize faster than the atoms re-condense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic energy into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. N. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons, and nitrogen compounds. The molecular dissociation completely removes the tissue structure, as opposed to ablation by dehydrating the tissue material by the removal of liquid within the cells of the tissue and extracellular fluids. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some modes of operation does not ablate such fatty tissue; however, the Coblation® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

Figure 2:
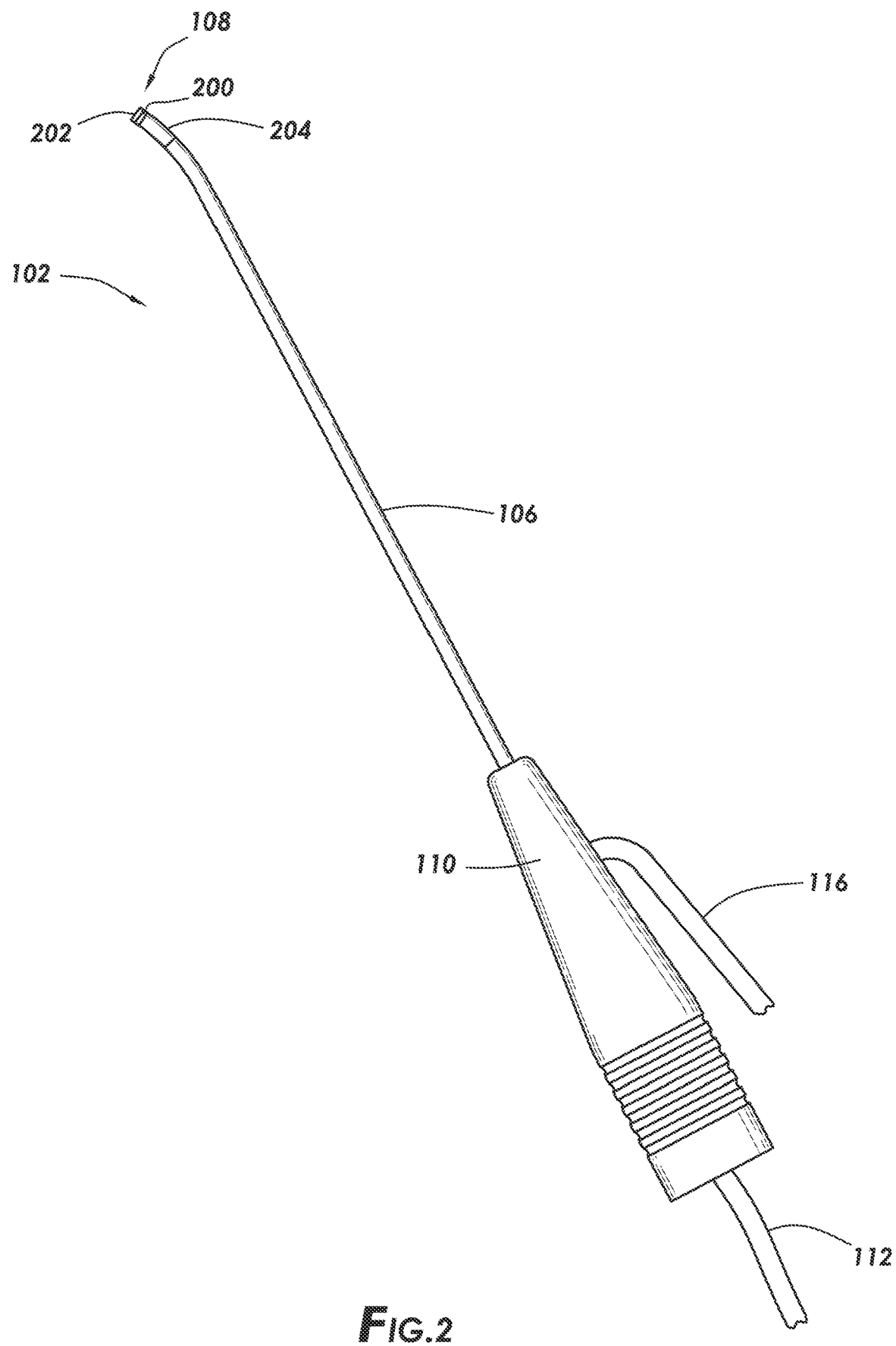
FIG. 2 shows an elevation view of wand in accordance with at least some embodiments.

FIG. 2 shows an elevation view of wand 102 in accordance with example systems. In particular, wand 102 comprises the elongate shaft 106 which may be flexible or rigid, the handle 110 is coupled to the proximal end of the elongate shaft 106, and an electrode support member 200 is coupled to the distal end of elongate shaft 106. Also visible in FIG. 2 is the flexible tubular member 116 and the flexible multi-conductor cable 112. The wand 102 comprises an active electrode 202 disposed on the distal end 108 of the elongate shaft 106. The active electrode 202 may be coupled to an active or passive control network within the controller 104 (FIG. 1) by means of one or more insulated electrical connectors (not shown) in the flexible multi-conductor cable 112. The active electrode 202 is electrically isolated from a common or return electrode 204 which is disposed on the shaft proximally of the active electrode 202, in some example systems within 1 millimeter (mm) to 25 mm of the distal tip. Proximally from the distal tip, the return electrode 204 is concentric with the elongate shaft 106 of the wand 102. The electrode support member 200 is positioned distal to the return electrode 204 and may be composed of an electrically insulating material such as epoxy, plastic, ceramic, silicone, glass or the like. Electrode support member 200 extends from the distal end 108 of elongate shaft 106 (e.g., about 1 to 20 mm) and provides support for active electrode 202.

Figure 3:
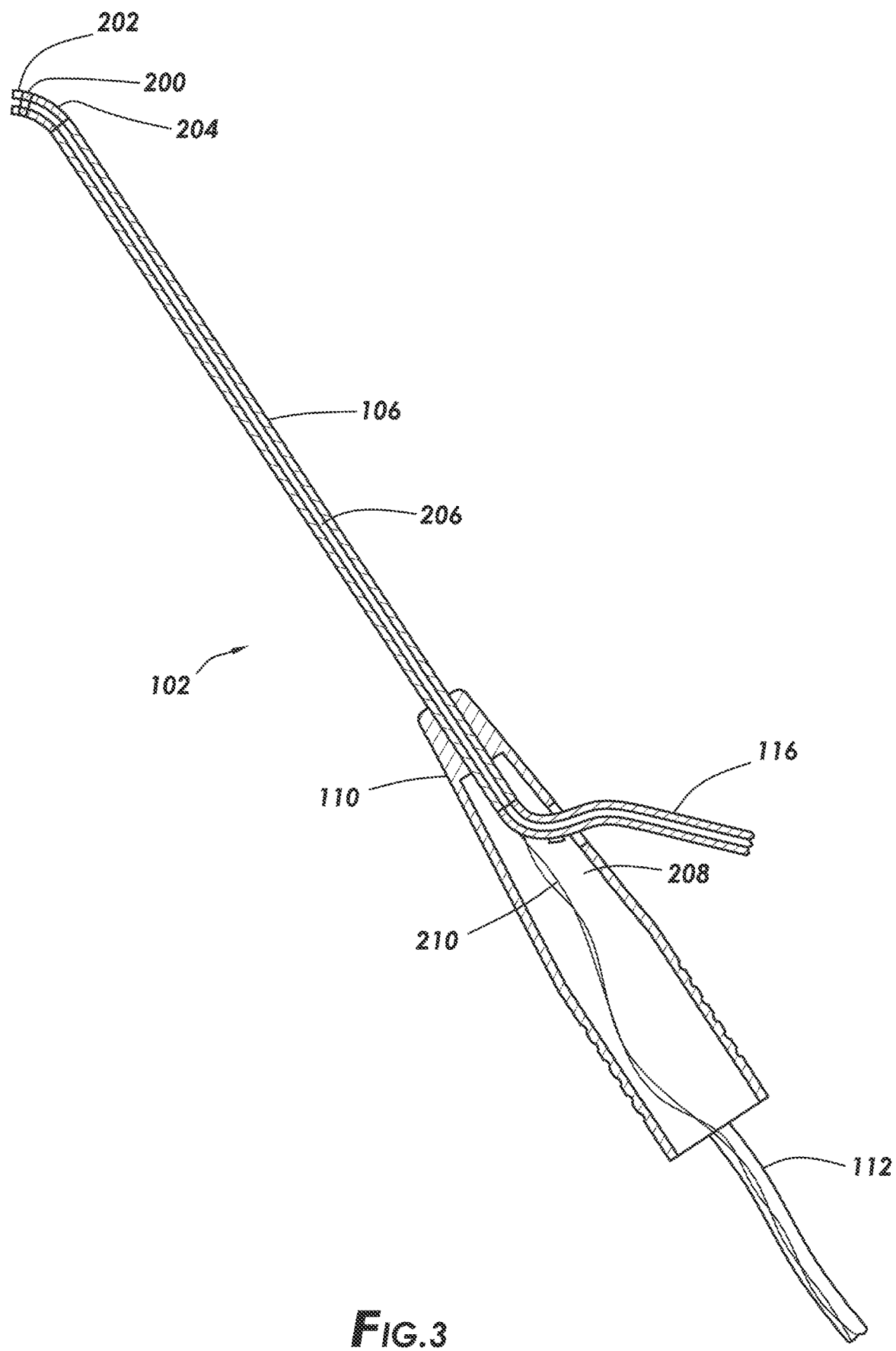
FIG. 3 shows a cross-sectional elevation view of the wand in accordance with at least some embodiments.

FIG. 3 shows a cross-sectional elevation view of the wand 102 in accordance with example embodiments. In particular, wand 102 comprises a lumen 206 defined within the elongate shaft 106. In the example wand 102 of FIG. 3, the inside diameter of the elongate shaft 106 defines the lumen 206, but in other cases a separate tubing within the elongate shaft 106 may define the lumen 206. In some cases the lumen 206 may be used for aspirating excess fluids, bubbles, tissue fragments, and/or products of ablation from the target site proximate to the active electrode 202. In other cases, the lumen 206 may be used to convey fluids (e.g., saline) to the surgical site. In the example system the lumen 206 extends into the handle 110 and is fluidly coupled to the flexible tubular member 116 for coupling to the peristaltic pump 118. Handle 110 also defines an inner cavity 208 within which electrical conductors 210 may reside, where the electrical conductors 210 may extend into the flexible multi-conductor cable 112 and ultimately couple to the controller 104. The electrical conductors likewise extend through the elongate shaft and couple, one each, to the return electrode 204 and the active electrode 202, but the electrical conductors 210 are not shown to reside within the elongate shaft 106 so as not to unduly complicate the figure.

Figure 4:
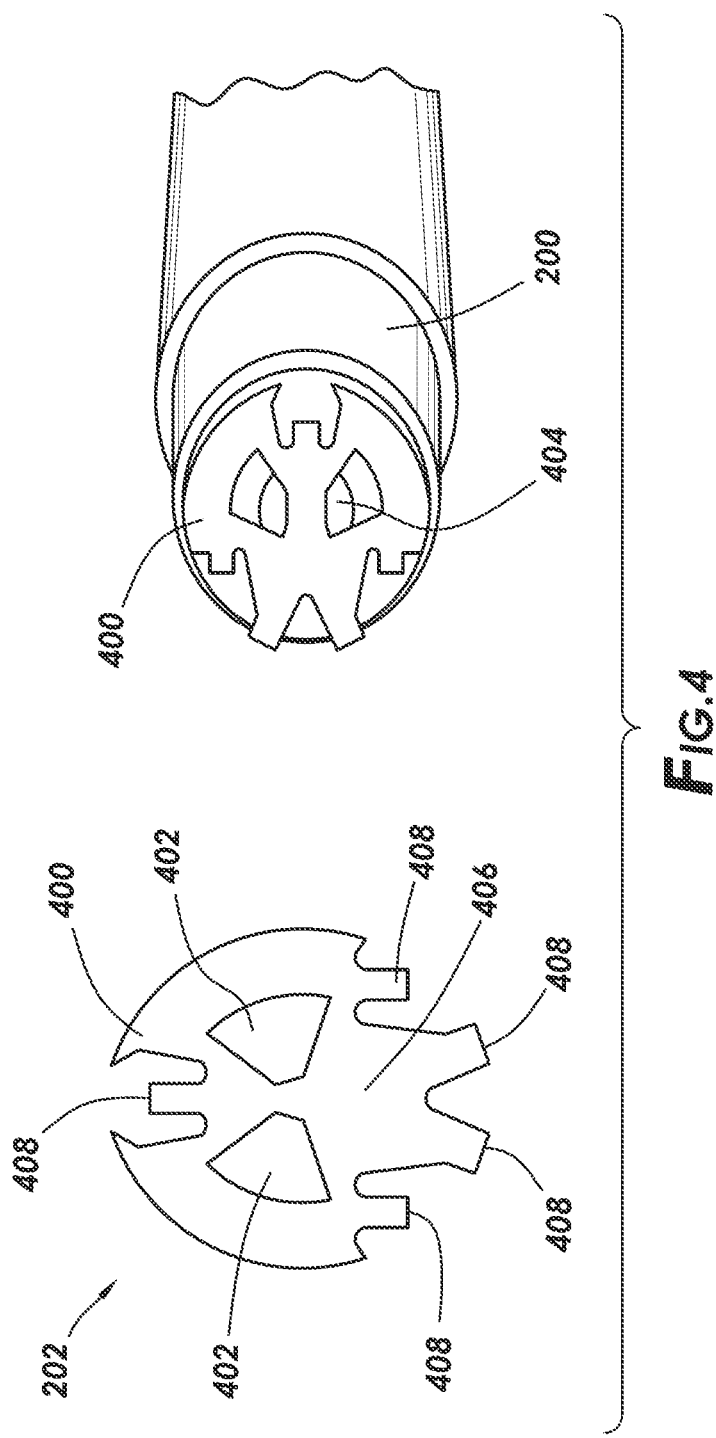
FIG. 4 shows both an elevation view and a perspective view of an example active electrode, in accordance with at least some embodiments.

FIG. 4 shows an elevation view of an example active electrode (on the left), as well as a perspective view of the distal end of wand 102 (on the right), in accordance with example systems. In particular, active electrode 202 may be an active screen electrode 400 as shown in FIG. 4. Screen electrode 400 may comprise a conductive material, such as tungsten, titanium, molybdenum, platinum, or the like. Screen electrode 400 may have a diameter in the range of about 0.5 to 8 mm, in some cases about 1 to 4 mm, and a thickness of about 0.05 to about 2.5 mm, in some cases about 0.1 to 1 mm. Screen electrode 400 may comprise a plurality of apertures 402 configured to rest over the distal opening 404 of suction lumen. Apertures 402 enable the passage of aspirated excess fluids, bubbles, and gases from the ablation site and are large enough to enable ablated tissue fragments to pass through into lumen 206 (FIG. 3). As shown, screen electrode 400 has an irregular shape which increases the edge to surface-area ratio of the screen electrode 400. A large edge to surface-area ratio increases the ability of screen electrode 400 to initiate and maintain a plasma layer in conductive fluid because the edges generate higher current densities, which a large surface area electrode tends to dissipate power into the conductive media.

In the example of FIG. 4, screen electrode 400 comprises a body 406 that rests over electrode support member 200 and the distal opening 404 to lumen 206. Screen electrode 400 further comprises tabs 408, in the example screen electrode 400 of FIG. 4, five tabs 408 are shown. The tabs 408 may rest on, be secured to, and/or be embedded in electrode support member 200. In certain embodiments, electrical connectors extend through electrode support member 200 and are coupled (i.e., via adhesive, braze, weld, or the like) to one or more of tabs 408 in order to secure screen electrode 400 to the electrode support member 200 and to electrically couple screen electrode 400 to controller 104 (FIG. 1). In example systems, screen electrode 400 forms a substantially planar tissue treatment surface for smooth resection, ablation, and sculpting of the meniscus, cartilage, and other tissues. In reshaping cartilage and meniscus, the surgeon often desires to smooth the irregular and ragged surface of the tissue, leaving behind a substantially smooth surface. For these applications, a substantially planar screen electrode treatment surface provides the desired effect. The specification now turns to a more detailed description of the controller 104.

The wand 102 as shown in FIGS. 1-4 is merely an example of a wand that may be used with the controller 104. Many other examples exist, including wands with multiple active electrodes, multiple return electrodes, and monopolar wands where the wand itself does not carry a return electrode. The surgeon selects a wand based on the surgical procedure to be performed. For example, while the wand 102 may be better suited for wet-field arthroscopic procedures, other wands (not specifically shown) may be selected and used for other procedures (e.g., tonsillectomies as an example of dry-field procedures). Thus, the example wand 102 as shown in FIGS. 1-4 should not be viewed as limiting.

The electrode circuit, including the plasma (when present), the fluid between the active and return electrode, the tissue between the active and return electrode, and the electrode-fluid interface, has or presents a certain amount of impedance to the flow of energy away from the active electrode and toward the return electrode or other return path. The impedance presented by the electrode circuit may be dependent on many factors, including, but not limited to: the thickness and volume of the plasma itself; the surface area of the active electrode not covered by a vapor layer and directly in contact with the conductive fluid; the volume flow of fluid and/or gasses away from the location of the plasma; the volume of fluid (e.g., blood, saline) in the current path; and the type and proximity of tissue proximate to the active and return electrodes.

The inventor of current application has discovered that plasma, tissue, bone, and fluids (e.g., blood, saline, extracellular fluid, intercellular fluid)—collectively electrosurgical entities—each have a characteristic frequency, or range of characteristic frequencies, better suited for detection of the presence of and/or state of each of the electrosurgical entities. Better control of an electrosurgical procedure may be implemented by measuring each electrosurgical entity at its respective characteristic frequencies. Example methods may thus comprise performing a first electrosurgical activity that causes a tissue-altering effect, the performing by way of first energy at a first frequency applied to an active electrode of an electrosurgical wand. Simultaneously with the tissue-altering effect, the example method may measure an electrosurgical parameter by way of a second energy at a second frequency applied to the active electrode of the electrosurgical, with the second frequency different than the first frequency. When the electrosurgical parameter measured at the second energy and second frequency shows changes are indicated, the example system may cease performing the first electrosurgical activity and perform a second electrosurgical activity that causes another tissue-altering effect, the performing by way of third energy at a third frequency applied to the active electrode. During the second electrosurgical activity, the example method may still measure at the second frequency. When the electrosurgical parameter measured by the second energy at the second frequency shows changes are again indicated, the example system may cease performing the second electrosurgical activity and perform again the first electrosurgical activity at the first energy and first frequency.

Consider, as an example, a surgeon using the controller 104 to perform an example plasma-based ablation (e.g., by way of an ablation energy having an ablation frequency). During the plasma-based ablation the example controller 104 may monitor bleeding by way of measurement energy having a measurement frequency (e.g., measuring impedance experienced at the surgical site by the measurement energy at the measurement frequency). In example cases, the ablation energy may be at an ablation frequency of about 100 kilo-Hertz (kHz), and the measurement frequency may be at a measurement frequency of about 50 kHz. In some cases the measurement energy may be lower than the ablation energy. In the example, when excess bleeding is detected by way of the measurement frequency, the controller 104 may cease the plasma-based ablation and switch to coagulation by way of a coagulation energy at a coagulation frequency applied to the active electrode. In some cases the coagulation energy may be lower than the ablation energy, and the coagulation frequency may be the same, higher, or lower than the ablation frequency. During the coagulation, the controller 104 may continue to monitor the state of bleeding by way of the measurement energy at the measurement frequency, and when the measurement indicates excess bleeding has ended, the controller 104 may switch back to the plasma-based ablation. The switching from the example plasma-based ablation, to coagulation, and back, may take place without action by the surgeon. In some cases switching from plasma-based ablation to coagulation and back may take place faster than can be perceived by the surgeon (e.g., switching from ablation to a coagulation for 100 milliseconds or less, and then switching back to ablation).

Consider, as another example, the surgeon using the controller 104 to perform the example plasma-based ablation (e.g., by way of the ablation energy at the ablation frequency). During the plasma-based ablation the example controller 104 may monitor the state of the plasma by way of the ablation energy at the ablation frequency (e.g., measuring impedance experienced by the ablation energy at the ablation frequency). The controller 104 may control the ablation energy and/or ablation frequency to maintain the plasma in a certain state or condition. For example, the controller 104 may control to a setpoint energy delivery to the surgical site at the ablation frequency. During the noted plasma-based ablation the example controller 104 may also monitor bleeding by way of the measurement energy at the measurement frequency (e.g., measuring impedance experienced by the measurement energy at the measurement frequency). As before, when excess bleeding is detected by way of the measurement frequency, the controller 104 may cease the ablation and switch to coagulation with a coagulation energy at a coagulation frequency. Again, during the coagulation the controller 104 may continue to monitor the state of bleeding by way of the measurement energy and measurement frequency, and when the measurement indicates excess bleeding has ended, the controller 104 may switch back to the plasma-based ablation.

Consider, as yet another example, the surgeon using the controller 104 to perform an example plasma-based ablation (e.g., by way of the ablation energy having at the ablation frequency) in a dry-field procedure. During the plasma-based ablation the example controller 104 may monitor the saline at the surgical site by way of measurement energy having a measurement frequency (e.g., measuring impedance experienced by the measurement energy at the measurement frequency). In example cases, the ablation energy may be at an ablation frequency of about 100 kHz, and the measurement frequency may be at a measurement frequency of about 50 kHz. In the example, when excess saline is detected by way of the measurement frequency, the controller 104 may control saline at the surgical site. Example controller 104 may control saline by increasing the suction flow rate by changing the motor speed of the peristaltic pump 118. In other cases, the flow rate of saline to the surgical site may be changed (e.g., lowered) by the controller 104. In yet still other cases, the controller may change both the flow rate of saline to the surgical site and the flow rate of saline away from the surgical site in response to detecting excess saline by way of the measurement energy at the measurement frequency.

Consider, as yet another example, a surgeon using the controller 104 to perform an example plasma-based ablation in a "blenderizer" mode (e.g., an ablation mode which modulates the voltage between a voltage that forms a plasma and a voltage that enables the plasma to collapse). The blenderizer mode may provide a slower cutting speed for the surgeon, with some concomitant coagulation. During the example blenderizer mode, the example controller 104 may nevertheless monitor bleeding by way of measurement energy having a measurement frequency (e.g., measuring impedance experienced at the surgical site by the measurement energy at the measurement frequency). In some cases the measurement energy may be lower than the blenderizer energy. In the example, when excess bleeding is detected by way of the measurement frequency, the controller 104 may cease the ablation in the blenderizer mode and switch to coagulation by way of a coagulation energy at a coagulation frequency applied to the active electrode. In some cases the coagulation energy may be lower than the ablation energy, and the coagulation frequency may be the same, higher, or lower than the ablation frequency. During the coagulation, the controller 104 may continue to monitor the state of bleeding by way of the measurement energy at the measurement frequency, and when the measurement indicates excess bleeding has ended, the controller 104 may switch back to the ablation in the blenderizer mode.

Consider, as yet another example, a surgeon using the controller 104 to perform an example coagulation at a first energy. During the example coagulation at the first energy, the example controller 104 may nevertheless monitor bleeding by way of measurement energy having a measurement frequency (e.g., measuring impedance experienced at the surgical site by the measurement energy at the measurement frequency). In the example, when excess bleeding is detected by way of the measurement frequency, the controller 104 may cease the coagulation at the first energy, and switch to coagulation at a second energy, the second energy higher than the first energy (and perhaps even at a different frequency). During the coagulation at the second energy, the controller 104 may continue to monitor the state of bleeding by way of the measurement energy at the measurement frequency, and when the measurement indicates excess bleeding has ended, the controller 104 may switch back to the coagulation at the first energy. The specification now turns to a more detailed discussion of an example controller 104.

Figure 5:
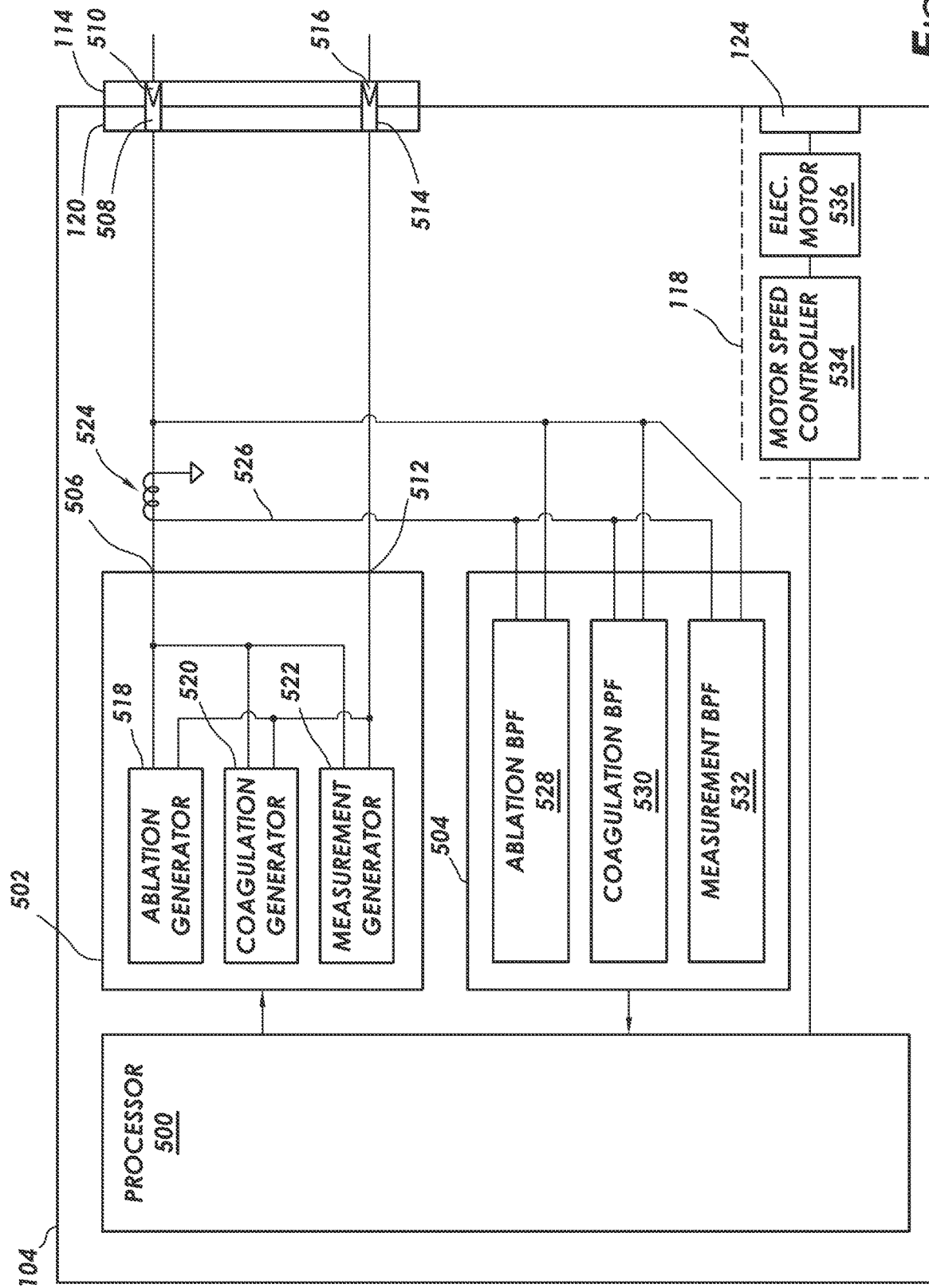
FIG. 5 shows an electrical block diagram of an electrosurgical controller in accordance with at least some embodiments.

FIG. 5 shows an electrical block diagram of controller in accordance with at least some embodiments. In particular, the controller 104 comprises a processor 500, an RF voltage generator 502, a filtering circuit 504, and the peristaltic pump 118. The RF voltage generator 502 defines an active connection or active lead 506 which is coupled to an active terminal 508 (e.g., electrical pin) in the controller connector 120. In use, an electrical pin 510 in the wand connector 114 is coupled to the active terminal 508, and the electrical pin 510 is coupled to the active electrode 202 (FIG. 2). Likewise, the RF voltage generator 502 defines a return connection or return lead 512 coupled to a return terminal 514 (e.g., electrical pin) in the controller connector 120. In use, an electrical pin 516 in the wand connector 114 is coupled to the return terminal 514, and the electrical pin 516 is coupled to the return electrode 204 (FIG. 2). Additional active terminals and/or return terminals may be used. The active terminal 508 is the terminal upon which the voltages and electrical currents are induced by the RF voltage generator 502, and the return terminal 514 provides a return path for electrical currents.

The example RF voltage generator 502 comprises an ablation generator 518, a coagulation generator 520, and a measurement generator 522. Each example generator 518, 520, and 522 defines an output and a return. As shown, the active outputs are electrically coupled together and define the active lead 506 of the overall RF voltage generator 502. Moreover, the returns are electrically coupled together and define the return lead 512 of the overall RF voltage generator 502. Thus, the output energy of each generator 518, 520, and 522 is effectively summed before being applied to the active terminal 508.

As the names imply, the example generators are designed and constructed to provide RF energy for a particular purpose. The example ablation generator 518 is configured to produce the ablation energy at the ablation frequency. For purposes of discussion, assume for now that the ablation generator 518 produces a sinusoidal signal at the ablation frequency. It may be possible to create a plasma with energy at any no-zero frequency, but in accordance with example embodiments the ablation frequency produced by the ablation generator 518 has a frequency between about 5 kHz and 20 Mega-Hertz (MHz), in some cases being between about 30 kHz and 2.5 MHz, in other cases being between about 50 kHz and 500 kHz, and some cases about 100 kHz.

The example coagulation generator 520 is configured to produce the coagulation energy at the coagulation frequency. Assume for now that the coagulation generator 520 produces a sinusoidal signal at the coagulation frequency. In accordance with example embodiments the coagulation frequency produced by the coagulation generator 520 may be between about 5 kHz and 20 MHz, in some cases being between about 30 kHz and 2.5 MHz, in other cases being between about 50 kHz and 500 kHz, and some cases about 100 kHz. Thus, the coagulation frequency may be the same or different than the ablation frequency, though in some cases the amount of energy provided to the surgical site by way of the coagulation generator 520 (i.e., the coagulation energy) may be lower than the energy provided to the surgical site by way of the ablation generator 518 (i.e., the ablation energy).

The example measurement generator 522 is configured to produce the measurement energy at the measurement frequency. Assume for now that the measurement generator 522 produces a sinusoidal signal at the measurement frequency. In accordance with example embodiments the measurement frequency produced by the measurement generator 522 has a frequency between about 60 Hertz and 20 MHz, in some cases being between about 5 kHz and 2.5 MHz, in other cases being between about 30 kHz and 500 kHz, and some cases about 50 kHz. The measurement frequency used by the measurement generator 522 depends on the electrosurgical parameter to be measured. For example, when the electrosurgical parameter of interest is blood or saline, the measurement frequency may be about 50 kHz, and the measurement frequency will be different than the ablation frequency and/or the coagulation frequency. Other measurement frequencies may be used depending on the electrosurgical parameter of interest. For example, if the electrosurgical parameter of interest is proximity of tissue to the active electrode, the measurement frequency may be 60 Hz. If the electrosurgical parameter of interest is proximity of bone to the active electrode, the measurement frequency may be different. In some cases the amount of energy provided to the surgical site by way of the measurement generator 522 (i.e., the measurement energy) may be lower than the ablation energy or the coagulation energy.

In example systems the processor 500 controls the RF voltage generator 502. More specifically, in example systems the processor 500 individually controls the ablation generator 518, the coagulation generator 520, and the measurement generator 522. In some cases, the processor 500 mutually exclusively commands the ablation generator 518 and the coagulation generator 520 to operate. That is, in some cases when the ablation generator 518 is active and providing energy to the surgical site, the coagulation generator 520 is inactive, and vice versa. In other cases, the ablation generator 518 and the coagulation generator 520 may be simultaneously active, but the processor 500 may selectively control the energy produced by each generator. For example, during ablation the ablation energy may be high and the coagulation energy may be low but non-zero, and during coagulation the coagulation energy may be high and the ablation energy may be low but non-zero. In example embodiments the measurement generator 522 is continuously active independent of the state of the ablation generator 518 and the coagulation generator 520. For example, when the measurement generator 522 is producing measurement energy tuned for sensing blood or saline at the surgical site, the measurement energy may be produced at all times regardless of the state of the ablation or coagulation.

Still referring to FIG. 5, the example controller 104 further comprises the filtering circuit 504. The example filtering circuit 504 is electrically coupled to the RF voltage generator 502. In particular, the example controller 104 defines a current sensing device, illustrative shown as a current transformer 524 defining sense lead 526. The "primary" of the current transformer 524 is the active lead 506, but in other cases the "primary" may be the return lead 512. The sense lead 526 of the example current transformer 524 is coupled to the filtering circuit 504. Thus, in operation of the controller 104 the filtering circuit 504 may sense current flow to the active terminal 508 and thus the active electrode 202 (FIG. 2). The example filtering circuit 504 shown also coupled directly to the active terminal 508 to sense the summed or combined voltage applied to the active terminal 508. Thus, in operation of the controller 104 the filtering circuit 504 may also sense the voltage applied to the active terminal 508 and thus active electrode 202. While FIG. 5 shows the filtering circuit 504 coupled directly to the active terminal 508, in other cases the voltage measurements may be electrically isolated, such as by way of an isolation transformer.

As discussed above, the example controller 104 is designed and constructed to sense one or more electrosurgical parameters. More particularly, the controller 104 is designed and constructed to measure impedance values experienced by energy at various frequencies. To that end, the example filtering circuit 504 comprises an ablation band-pass filter 528 ("Ablation BPF" in the figure), a coagulation band-pass filter 530 ("Coagulation BPF" in the figure), and a measurement band-pass filter 532 ("measurement BPF" in the figure). The ablation band-pass filter 528 is designed and constructed to pass a current signal indicative of or proportional to current flow at the ablation frequency, and designed and constructed to pass a voltage signal indicative of or proportional to voltage at the ablation frequency. Other frequencies are blocked by the ablation band-pass filter 528. Stated otherwise, the center frequency of the ablation band-pass filter 528 may be the ablation frequency (e.g., 100 kHz). The processor 500, in turn receives the current signal and voltage signal, and calculates an impedance value associated with the ablation energy. For example, the processor 500 may digitize the current signal and voltage signal passed by the ablation band-pass filter 528, and based thereon calculate the both the real and imaginary components of the complex impedance value at the ablation frequency. In other cases, the processor 500 may digitize the current signal and voltage signal passed by the ablation band-pass filter 528, and based thereon calculate just the real component of the impedance at the ablation frequency. Before proceeding, it will be understood sensing current and voltage associated with the ablation need not be implemented in all cases, and thus the ablation band-pass filter 528 and related functionality need not be present in every case.

The example filtering circuit 504 may also comprise the coagulation band-pass filter 530. The coagulation band-pass filter 530 is designed and constructed to pass a current signal indicative of or proportional to current flow at the coagulation frequency, and designed and constructed to pass a voltage signal indicative of or proportional to voltage at the coagulation frequency. Other frequencies are blocked by the coagulation band-pass filter 530. Stated otherwise, the center frequency of the coagulation band-pass filter 530 may be the coagulation frequency. The processor 500, in turn receives the current signal and voltage signal, and calculates an impedance value associated with the coagulation energy. For example, the processor 500 may digitize the current signal and voltage signal passed by the coagulation band-pass filter 530, and based thereon calculate the both the real and imaginary components of the complex impedance value at the coagulation frequency. In other cases, the processor 500 may digitize the current signal and voltage signal passed by the coagulation band-pass filter 530, and based thereon calculate just the real component of the impedance at the coagulation frequency.

A couple of points to consider before proceeding. In some cases the ablation frequency and coagulation frequency are the same. Switching between ablation and coagulation may involve reducing ablation energy (e.g., reducing to zero) to enable the plasma to collapse, and then increasing the energy (at the same frequency) to perform coagulation, with the coagulation energy lower than the ablation energy. Thus, while the example controller 104 shows both an ablation band-pass filter 528 and a coagulation band-pass filter 530, in some cases a single band-pass filter system may be used to sense the state of both tissue-altering effects. Further, it will be understood sensing current and voltage associated with the coagulation need not be implemented in all cases, and thus the coagulation band-pass filter 530 and related functionality need not be present in every case.

Still referring to FIG. 5, the example filtering circuit 504 also comprises the measurement band-pass filter 532. The measurement band-pass filter 532 is designed and constructed to pass a current signal indicative of or proportional to current flow at the measurement frequency, and designed and constructed to pass a voltage signal indicative of or proportional to voltage at the measurement frequency. Other frequencies are blocked by the coagulation band-pass filter 530. Stated otherwise, the center frequency of the measurement band-pass filter 532 may be the measurement frequency. Because of the relationship of the characteristic frequencies of the electrosurgical parameters, the measurement band-pass filter 532 may alternatively be implemented as a low-pass filter having a cutoff frequency that enables the measurement frequency and lower frequencies to pass. Regardless of the precise nature of the measurement band-pass filter 532, the processor 500 receives the current signal and voltage signal, and calculates an impedance value associated with the measurement energy. For example, the processor 500 may digitize the current signal and voltage signal passed by the measurement band-pass filter 532, and based thereon calculate the both the real and imaginary components of the complex impedance value at the measurement frequency. In other cases, the processor 500 may digitize the current signal and voltage signal passed by the measurement band-pass filter 532, and based thereon calculate just the real component of the impedance at the measurement frequency.

Having introduced an example controller 104, the specification now turns again to examples of operation. Consider a surgeon using the controller 104 of FIG. 5 to perform a plasma-based ablation (e.g., by way of an ablation energy having an ablation frequency). During the plasma-based ablation the processor 500 commands the ablation generator 518 to produce ablation energy at the ablation frequency (e.g., 100 kHz). Also during the plasma-based ablation the processor 500 commands the measurement generator 522 to produce measurement energy at the measurement frequency (e.g., 50 kHz). The example controller 104 may monitor bleeding by way of measurement energy at the measurement frequency. That is, the processor 500 may receive signals indicative of or proportional to the measurement current and the measurement voltage at the measurement frequency by way of the measurement band-pass filter 432. The processor 500 may thus calculate an impedance experienced by the measurement energy, where the magnitude of the impedance is indicative of presence of blood at the surgical site. When excess bleeding is detected by the processor 500 way of the measurement frequency, the processor 500 may command the ablation generator 518 to reduce or cease producing ablation energy, and command the coagulation generator 520 to produce coagulation energy at the coagulation frequency. During the coagulation, the processor 500 may continue to monitor the state of bleeding by way of the measurement energy at the measurement frequency, and when the impedance experienced by the measurement energy indicates excess bleeding has ended, the processor 500 may command the coagulation generator 520 to reduce or cease producing coagulation energy, and command the ablation generator 518 to resume or increase ablation energy. The switching from the example plasma-based ablation, to coagulation, and back, may take place without action by the surgeon.

In addition to the example above of monitoring for excess bleeding, during the plasma-based ablation the example the processor 500 may monitor state of the plasma by way of the ablation energy at the ablation frequency (e.g., measuring impedance experienced by the ablation energy at the ablation frequency). That is, the processor 500 may receive signals indicative of or proportional to the ablation current and the ablation voltage at the ablation frequency from the ablation band-pass filter 528. The processor 500 may thus calculate and impedance experienced by the ablation energy, where the magnitude of the impedance is indicative of the presence or state of the plasma at the surgical site. The processor 500 may control the ablation energy and/or ablation frequency to maintain the plasma in a certain state or condition (e.g., controlling to a setpoint energy delivery at the ablation frequency).

Consider, as yet another example, the surgeon using the controller 104 of FIG. 5 to perform an example plasma-based ablation (e.g., by way of the ablation energy having at the ablation frequency) in a dry-field procedure. During the plasma-based ablation the processor 500 commands the ablation generator 518 to produce ablation energy at the ablation frequency (e.g., 100 kHz). Also during the plasma-based ablation the processor 500 commands the measurement generator 522 to produce measurement energy at the measurement frequency (e.g., 50 kHz). The example controller 104 may monitor saline at the surgical site by way of measurement energy at the measurement frequency by way of the measurement band-pass filter 532. That is, the processor 500 may receive signals indicative of or proportional to the measurement current and the measurement voltage at the measurement frequency. The processor 500 may thus calculate an impedance experienced by the measurement energy, where the magnitude of the impedance is indicative of presence of saline at the surgical site. When excess saline is detected by the processor 500 way of the measurement frequency, the processor 500 may command a change in the speed of the peristaltic pump 118. In particular, the processor 500 may communicate with the motor speed controller 534 a speed command, and in turn the motor speed controller 534 changes the speed of the electric motor 536 that turns the rotor 124. In cases where the peristaltic pump 118 controls flow of saline away from the surgical site, when excess saline is detected the processor 500 may increase the speed of the peristaltic pump, thus increasing the flow of saline away from the surgical site. In yet still other cases, the processor 500 may command external devices responsive to detecting excess saline, such as command an inflow flow to reduce flow of saline to the surgical site. The description now transitions to an alternative controller.

Figure 6:
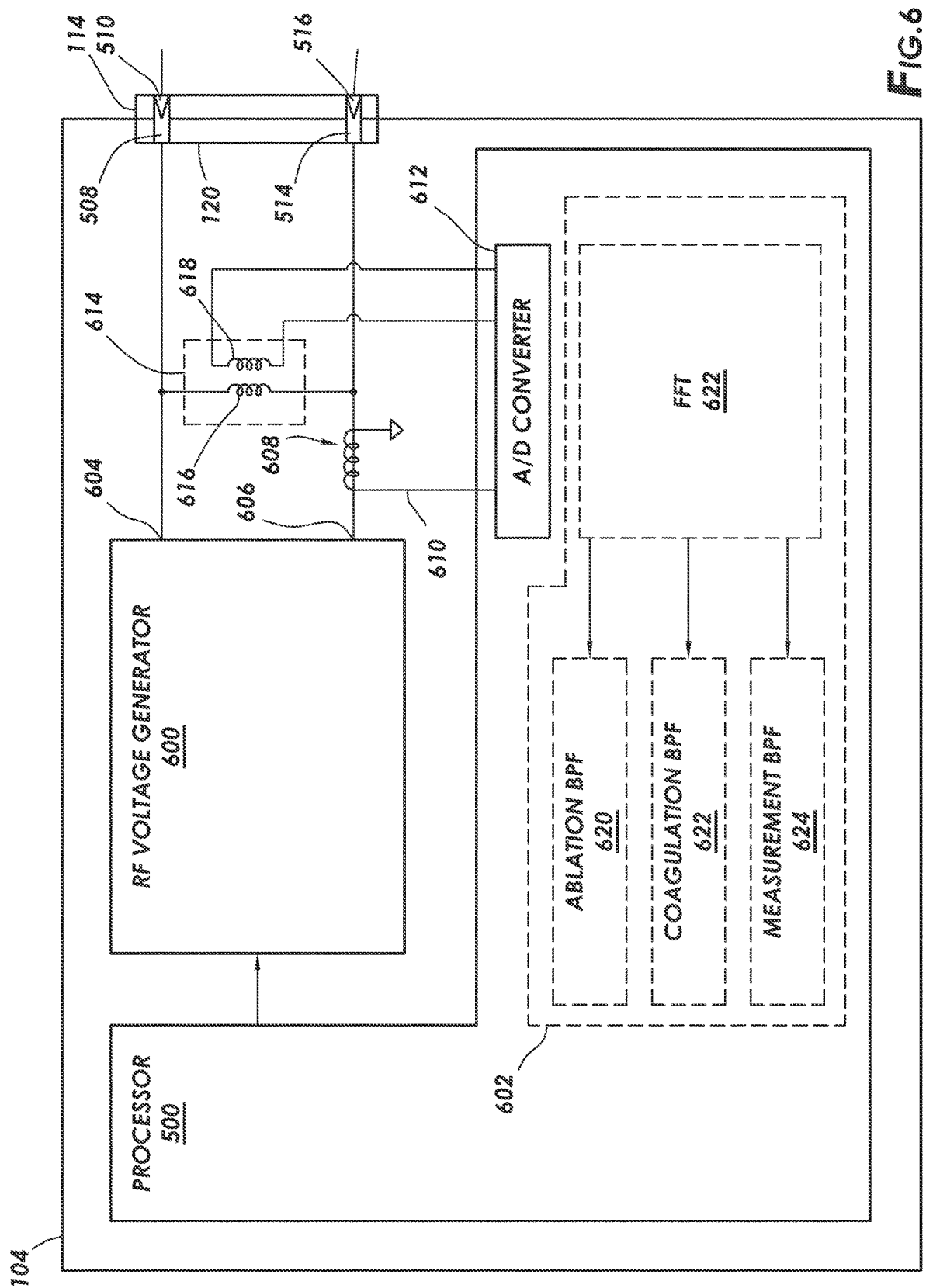
FIG. 6 shows an electrical block diagram of an electrosurgical controller in accordance with at least some embodiments.

FIG. 6 shows an electrical block diagram of an electrosurgical controller in accordance with at least some embodiments. The controller 104 of FIG. 6 shows alternative implementations of the RF voltage generator and the filtering. In particular, the controller 104 comprises the processor 500, an RF voltage generator 600, and a filtering system (hereafter just filtering 602) illustratively implemented as software within the processor 500. The peristaltic pump has been omitted so as not to further complicate the figure, but may nevertheless be present in some embodiments.

As before, the RF voltage generator 600 defines an active connection or active lead 604 coupled to an active terminal 508 (e.g., electrical pin) in the controller connector 120. In use, the electrical pin 510 in the wand connector 114 is coupled to the active terminal 508, and the electrical pin 510 is coupled to the active electrode 202 (FIG. 2). Likewise, the RF voltage generator 600 defines a return connection or return lead 606 coupled to the return terminal 514 (e.g., electrical pin) in the controller connector 120. In use, the electrical pin 516 in the wand connector 114 is coupled to the return terminal 514, and the electrical pin 516 is coupled to the return electrode 204 (FIG. 2). Additional active terminals and/or return terminals may be used. The active terminal 508 is the terminal upon which the voltages and electrical currents are induced by the RF voltage generator 600, and the return terminal 514 provides a return path for electrical currents.

The description of the example controller 104 of FIG. 5 assumed that each of the ablation generator 518, the coagulation generator 520, and the measurement generator 522 produced a sinusoidal waveform at respective frequencies. The sinusoidal waveforms were effectively summed and applied to the active terminal 508. In FIG. 6, however, separate generators are not specifically needed, yet the example system may still perform the various impedance measurements at the various frequencies. That is, unlike the RF voltage generator 502, the RF voltage generator 600 does not implement separate sub-generators to create the combined signal.

The example RF voltage generator 600 produces a square-wave signal. The peak-to-peak voltage generated by the RF voltage generator 600 may have a peak-to-peak voltage in the range of 10 V to 2000 V, in some cases in the range of 100 V to 1800 V, in other cases in the range of about 28 V to 1200 V, and often in the range of about 100 V to 320 V peak-to-peak. The duty cycle of a square-wave signal produced by the RF voltage generator 600 is on the order of about 50% for some embodiments. Although square waves are generated and provided in the example embodiments, the square-wave signal is modifiable to include features such as voltage spikes in the leading or trailing edges of each half-cycle. The RF voltage generator 600 delivers average power levels ranging from several milliwatts to hundreds of watts per electrode, depending on parameters of the ablation and state of the plasma proximate to the active electrode. A description of example RF voltage generators can be found in commonly assigned U.S. Pat. Nos. 6,142,992 and 6,235,020, the complete disclosure of both patents are incorporated herein by reference for all purposes. Reference is also made to commonly assigned U.S. Pat. No. 8,257,350, entitled "Method And System of an Electrosurgical Controller With Wave-Shaping", the complete disclosure of which is incorporated herein by reference as if reproduced in full below.

In spite of the RF voltage generator 600 producing a square-wave signal, the various embodiments of performing electrosurgical activities with energy at certain frequencies, and simultaneously measuring electrosurgical parameters other frequencies, may still take place. In particular, any time-varying periodic signal may be produced or reproduced by summing various sinusoidal signals. Stated otherwise, any time-varying periodic signal may be considered to be a sum of various sinusoidal signals. This fundamental relationship is the basis of several mathematical concepts, such as Fourier Transforms, where Fourier Transforms may be used to represent any signal from the time domain in the frequency domain. Consider a square-wave signal that defines a frequency between any two consecutive similar features (e.g., leading edges) and a duty cycle. The square-wave signal, from the perspective of the frequency domain, may be considered to be the sum of a first sinusoidal signal at the fundamental frequency with a first amplitude, a second sinusoidal signal at twice the fundamental frequency with a second amplitude, a third sinusoidal signal at thrice the fundamental frequency with a third amplitude, and so on. It follows that the RF voltage generator 600, in producing a square-wave signal, can be considered to be creating a summed signal comprising sinusoidal signals at the fundamental frequency, twice the fundamental frequency, thrice the fundamental frequency, and so on. Thus, the example RF voltage generator 600, in creating the square-wave signal, can be considered to be creating ablation energy at the ablation frequency (e.g., all frequencies at twice the fundamental frequency and above), and further can be considered to be creating the measurement energy at the measurement frequency (e.g., at the fundamental frequency).

Still referring to FIG. 6, the example controller 104 further comprises the filtering 602. Unlike FIG. 5 where the filtering circuit is a physical set of electrical filters, in the example controller 104 of FIG. 6 the filtering 602 may be implemented in software within the processor 500 as shown. Performing the filtering 602 in software within the processor 500 is not tied to the RF voltage generator 600 of FIG. 6 producing the example square-wave signal; rather, performing the filtering 602 in software within the processor 500 may be used with any RF voltage generator system, including the RF voltage generator 502 of FIG. 5.

The example filtering 602 is coupled to the RF voltage generator 600. In particular, the example controller 104 defines a current sensing device, illustrative shown as current transformer 608 defining sense lead 610. The "primary" of the current transformer 608 is the return lead 606, but in other cases the "primary" may be the active lead 604. The sense lead 610 of the example current transformer 608 is coupled to the filtering 602. In particular, the sense lead 610 couples to processor 500, and thus the filtering 602, by way of an analog-to-digital converter 612. In cases where the processor 500 is a microcontroller and/or ASIC, the analog-to-digital converter 612 may be an integral component with the processor 500 as shown; however, in other cases the analog-to-digital converter 612 may be a stand-alone device communicatively coupled to the processor 500. In operation of the controller 104 of FIG. 6, the filtering 602 may sense current associated with the active terminal 508 (through the return) and thus active electrode 202 (FIG. 2).

The example filtering 602 also coupled to the active terminal 508 to sense the voltage applied to the active terminal 508. In particular, in the example controller 104 of FIG. 6 uses an isolation transformer 614 to sense the voltage applied to the active terminal. The example isolation transformer 614 defines a primary winding 616 coupled across the active lead 604 and the return lead 606. The example isolation transformer 614 further defines a secondary winding 618 magnetically coupled to the primary winding 616. Thus, in operation of the controller 104 of FIG. 6 the filtering 602 may also sense voltage applied to the active terminal 508 and thus active electrode 202 (FIG. 2), by way of the example analog-to-digital converter 612. Utilizing the isolation transformer 614 of FIG. 6 is not tied to the RF voltage generator 600 or the filtering 602 implemented within the processor 500. The isolation transformer 614 may be used with any RF voltage generator system and any filtering system.

As before, the example controller 104 of FIG. 6 is designed and constructed to sense one or more electrosurgical parameters. More particularly, the controller 104 of FIG. 6 is designed and constructed to measure impedance values experienced by energy at various frequencies. To that end, the example filtering 602 comprises an ablation band-pass filter 620 ("Ablation BPF" in the figure), a coagulation band-pass filter 622 ("Coagulation BPF" in the figure), and a measurement band-pass filter 624 ("Measurement BPF" in the figure). The ablation band-pass filter 620 is designed and constructed to digitally pass a current signal indicative of or proportional to current flow at the ablation frequency, and designed and constructed to digitally pass a voltage signal indicative of or proportional to voltage at the ablation frequency. Other frequencies are digitally blocked by the ablation band-pass filter 528. Stated otherwise, the center frequency of the ablation band-pass filter 528 may be the ablation frequency (e.g., 100 kHz). The processor 500, thus receives a digital representation of a current signal and a voltage signal, and calculates an impedance value associated with the ablation energy. Before proceeding, and as before, it will be understood sensing current and voltage associated with the ablation need not be implemented in all cases, and thus the ablation band-pass filter 528 and related functionality need not be present in every case.

The example filtering 602 may also comprise the coagulation band-pass filter 622. The coagulation band-pass filter 622 is designed and constructed to digitally pass a current signal indicative of or proportional to current flow at the coagulation frequency, and designed and constructed to digitally pass a voltage signal indicative of or proportional to voltage at the coagulation frequency. Other frequencies are digitally blocked by the coagulation band-pass filter 530. Stated otherwise, the center frequency of the coagulation band-pass filter 530 may be the coagulation frequency. The processor 500, in turn receives a digital representation of the current signal and voltage signal, and calculates an impedance value associated with the coagulation energy.

As before, in some cases the ablation frequency and coagulation frequency are the same. Switching between ablation and coagulation may thus involve reducing ablation energy (e.g., reducing to zero) to enable the plasma to collapse, and then increasing the energy (at the same frequency) to perform coagulation, with the coagulation energy being lower than the ablation energy. Thus, while the example controller 104 of FIG. 6 shows both an ablation band-pass filter 620 and a coagulation band-pass filter 622, in some cases a single band-pass filter may be used to sense the state of both tissue-altering effects. Further, it will be understood sensing current and voltage associated with the coagulation need not be implemented in all cases, and thus the coagulation band-pass filter 622 and related functionality need not be present in every case.

Still referring to FIG. 6, the example filtering 602 also comprises the measurement band-pass filter 624. The measurement band-pass filter 624 is designed and constructed to digitally pass a current signal indicative of or proportional to current flow at the measurement frequency, and designed and constructed to digitally pass a voltage signal indicative of or proportional to voltage at the measurement frequency. Other frequencies are digitally blocked by the coagulation band-pass filter 622. Stated otherwise, the center frequency of the measurement band-pass filter 624 may be the measurement frequency. Because of the relationship of the characteristic frequencies of the electrosurgical parameters, the measurement band-pass filter 624 may alternatively be implemented as a low-pass filter having a cutoff frequency that enables the measurement frequency and lower frequencies to pass. Regardless of the precise nature of the measurement band-pass filter 624, the processor 500 receives digital representations of the current signal and voltage signal, and calculates an impedance value associated with the measurement energy.

The example filtering 602 of FIG. 6 is further shown to include a block for Fourier Transform of the digital representations of the analog signals. In particular, the example filtering 602 includes a fast-Fourier Transform (FFT) block 626 couple between the example analog-to-digital converter 612 and the various band-pass filters. As the name implies the FFT block 626 may take perform a Fourier Transform (such as a fast-Fourier Transform) of the current and voltage signals produced by the RF voltage generator 600, and supply the FFT to each of the band-pass filters 620, 622, and 624. The band-pass filters 620, 622, and 624, in turn, extract their frequency or frequencies of interest, and pass the resultant on to other programs executed by the processor 500 to perform impedance calculating and to implement control actions based thereon.

The specification now turns again to examples of operation. Consider, a surgeon using the controller 104 of FIG. 6 to perform a plasma-based ablation. During the plasma-based ablation the processor 500 commands the RF voltage generator 600 to produce the square-wave signal, and a component of the square-wave signal comprises the ablation energy at the ablation frequency (e.g., 100 kHz). Another component of the example square-wave signal comprises the measurement energy at the measurement frequency (e.g., 50 kHz). The example controller 104 may monitor bleeding by way of measurement energy at the measurement frequency. That is, the processor 500 may receive from the filtering 602 digital representations of signals indicative of or proportional to the measurement current and the measurement voltage at the measurement frequency. The processor 500 may thus calculate and impedance experienced by the measurement energy, where the magnitude of the impedance is indicative of presence of blood at the surgical site. When excess bleeding is detected by the processor 500 way of the measurement frequency, the processor 500 may command the RF voltage generator 600 to reduce amplitude (e.g., reduce the amplitude to zero) of the square-wave signal to extinguish the plasma. Reducing amplitude of the example square-wave signal may likewise reduce the measurement energy at the measurement frequency. Once the plasma is extinguished, the processor 500 may command the RF voltage generator 600 to produce the square-wave signal at a particular amplitude to perform coagulation, and again the square-wave signal may be considered to have a component comprising the measurement energy at the measurement frequency. During the coagulation, the processor 500 may continue to monitor the state of bleeding by way of the measurement energy and measurement frequency, and when the impedance experienced by the measurement energy indicates excess bleeding has ended, the processor 500 may command the coagulation generator 520 to increase the amplitude of the square-wave signal to again ignite the plasma to continue the example plasma-based ablation. The switching between from the plasma-based ablation, to coagulation, and back, may take place without action by the surgeon.

In addition to the example of above of monitoring for excess bleeding, during the plasma-based ablation the example the processor 500 may monitor state of the plasma by way of the ablation energy at the ablation frequency (e.g., measuring impedance experienced by the ablation energy at the ablation frequency). That is, the processor 500 may receive digital representations of signals indicative of or proportional to the ablation current and the ablation voltage at the ablation frequency. The processor 500 may thus calculate and impedance experienced by the ablation energy, where the magnitude of the impedance is indicative of the presence or state of the plasma at the surgical site. The processor 500 may control the ablation energy (e.g., by controller amplitude of the square-wave signal) to maintain the plasma in a certain state or condition (e.g., controlling to a setpoint energy delivery at the ablation frequency). The example system of FIG. 6 works equivalently for dry-field procedures.

Figure 7:
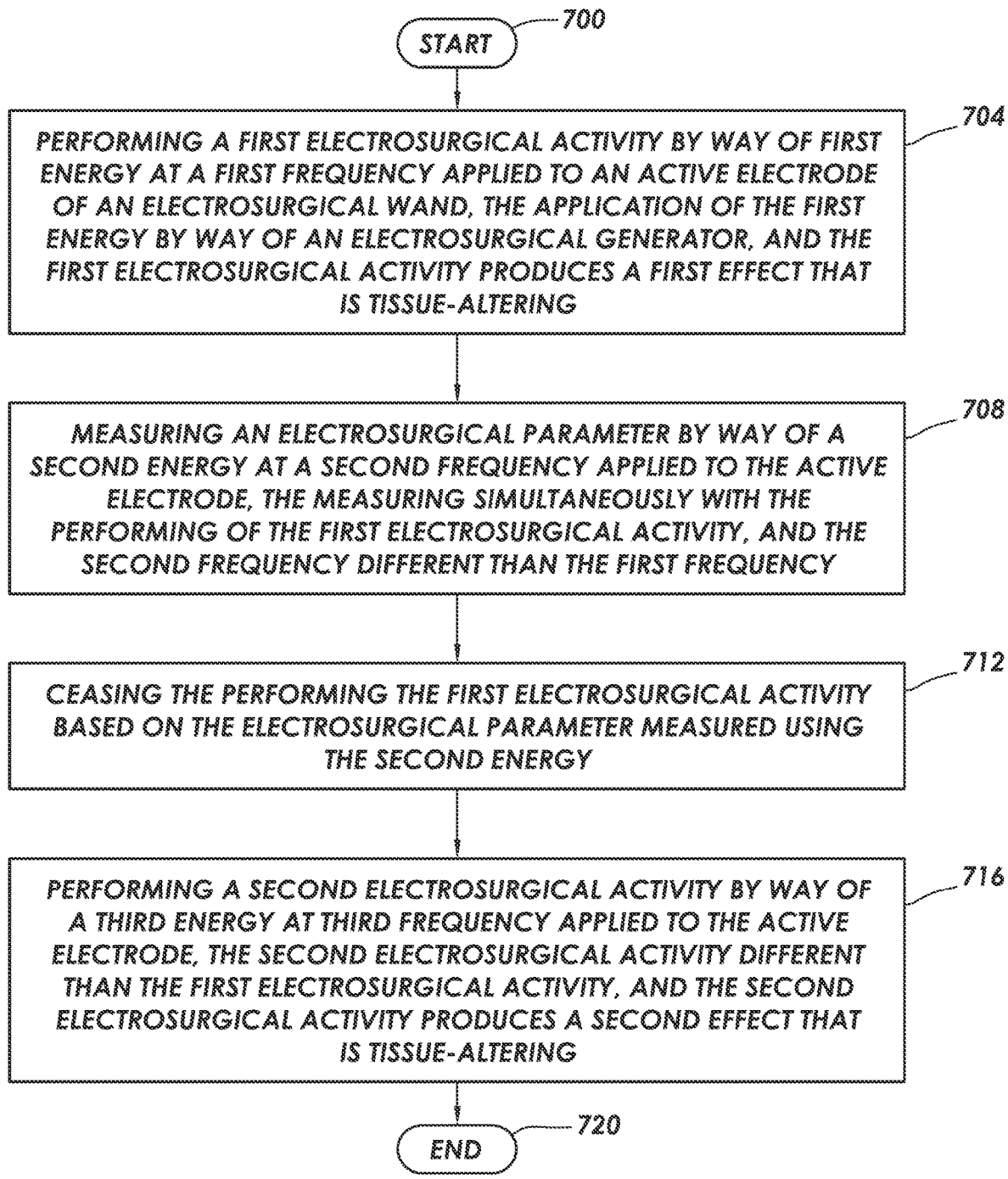
FIG. 7 shows a method in accordance with at least some embodiments.

FIG. 7 shows a method in accordance with at least some embodiments. In particular, the method starts (block 700) and comprises: performing a first electrosurgical activity by way of first energy at a first frequency applied to an active electrode of an electrosurgical wand, the application of the first energy by way of an electrosurgical generator, and the first electrosurgical activity produces a first effect that is tissue-altering (block 704); measuring an electrosurgical parameter by way of a second energy at a second frequency applied to the active electrode, the measuring simultaneously with the performing of the first electrosurgical activity, and the second frequency different than the first frequency (block 708); ceasing the performing the first electrosurgical activity based on the electrosurgical parameter measured using the second energy (block 712); performing a second electrosurgical activity by way of a third energy at third frequency applied to the active electrode, the second electrosurgical activity different than the first electrosurgical activity, and the second electrosurgical activity produces a second effect that is tissue-altering (block 716). Thereafter the method ends (block 720), likely to be immediately restarted.

Figure 8:
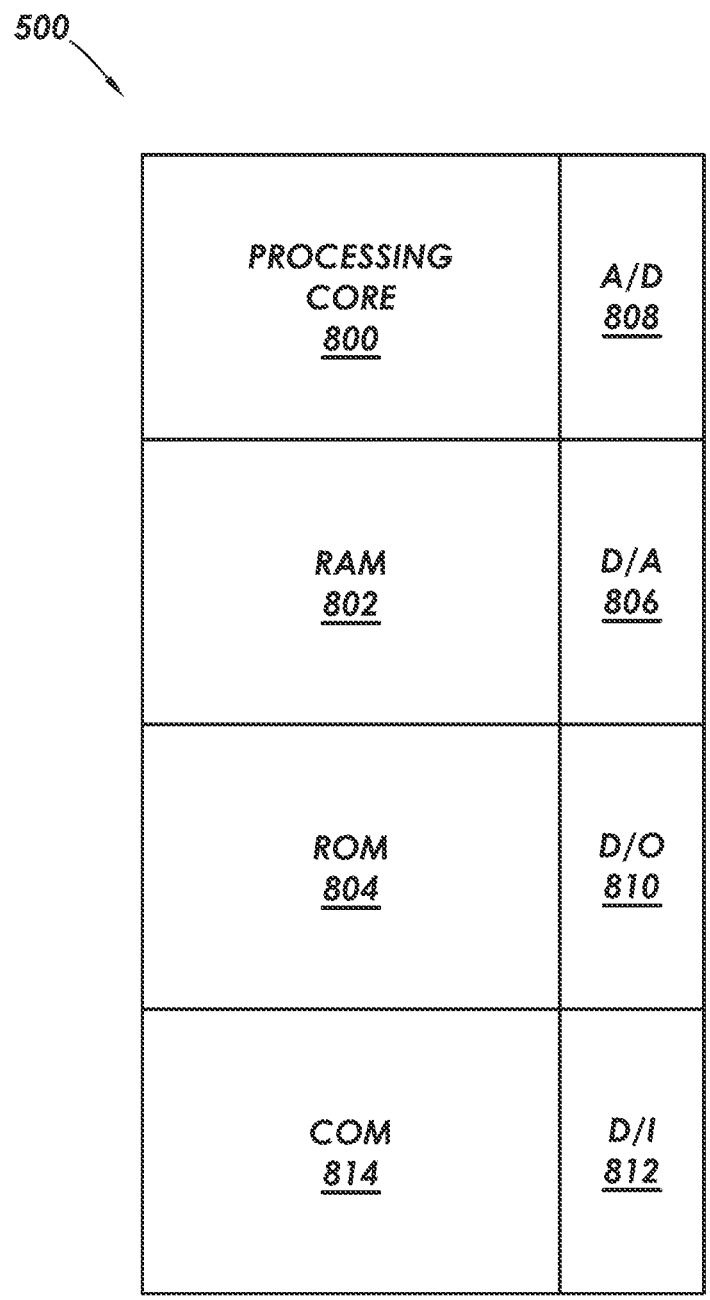
FIG. 8 shows a processor in accordance with at least some embodiments.

FIG. 8 shows a processor in accordance with at least some embodiments. The processor 500 may be a microcontroller, and therefore the microcontroller have a processing core 800 integral with random access memory (RAM) 802, read-only memory (ROM) 804, a digital-to-analog converter (D/A) 806, an analog-to-digital converter (A/D) 808 (e.g., which could be the analog-to-digital converter 612 of FIG. 6), digital outputs (D/O) 810, and digital inputs (D/I) 812. The processor 500 may further provide one or more externally available peripheral busses (not specifically shown), such as a serial bus (e.g., I²C), parallel bus, or other bus and corresponding communication mode. The processor 500 may further be integral with communication logic 814 to enable the processor 500 to communicate with external devices, as well as internal devices, such as interface device 130 of FIG. 1. Although in some embodiments the processor 500 may be implemented in the form of a microcontroller, in other embodiments the processor 500 may be implemented as a standalone processing core in combination with individual RAM, ROM, communication, ND, D/A, D/O, and D/I devices, as well as communication hardware for communication to peripheral components.

ROM 804 stores instructions executable by the processing core 800. In particular, the ROM 804 may comprise a software program that, when executed, causes the controller to implement the example method of FIG. 7. The RAM 802 may be the working memory for the processing core 800, where data may be temporarily stored and from which instructions may be executed. Processor 500 couples to other devices within the various example controllers 104 by way of the digital-to-analog converter 806 (e.g., in some embodiment the voltage generators), digital outputs 810 (e.g., in some embodiment the voltage generators), digital inputs 812 (e.g., interface devices such as buttons 132 or foot pedal assembly 134 of FIG. 1), and communication logic 814 (e.g., interface device 130 of FIG. 1).

The above discussion is meant to be illustrative of the principles and various embodiments of the present invention. Numerous variations and modifications are possible. It is intended that the following claims be interpreted to embrace all such variations and modifications.

What is claimed:

1. An electrosurgical controller for an electrosurgical wand, the electrosurgical controller comprising:

an active terminal configured to couple to an active electrode of an electrosurgical wand, and a return terminal;

a voltage generator configured to create and supply to the active electrode a combined energy comprising an ablation energy at an ablation frequency and a sensing energy at a sensing frequency, the ablation frequency different than the sensing frequency, the sensing energy supplied at a same time as the ablation energy, and the voltage generator configured to apply the combined energy including both the ablation energy and the sensing energy to the active electrode of the electrosurgical wand;

a sensing circuit coupled to the voltage generator, the sensing circuit configured to sense, from the combined energy comprising both the ablation energy and the sensing energy, (i) a sense current associated with the sensing frequency and (ii) an ablation current associated with the ablation frequency; and a processor coupled to the voltage generator and the sensing circuit, the processor configured to:

select the sensing frequency based on which electrosurgical parameter of interest is to be measured, wherein the electrosurgical parameter of interest is an amount of bleeding at a surgical site, an amount of saline at a surgical site, a proximity of tissue to the active electrode, or a proximity of bone to the active electrode, wherein the sensing frequency is different for each of the respective electrosurgical parameters except for the amount of bleeding at the surgical site and the amount of saline at the surgical site;

calculate a control impedance experienced by the sensing energy at the sensing frequency based on the sense current;

command the voltage generator to change a parameter of the ablation energy at the ablation frequency based on the control impedance; and in response to a determination, from the sensing energy, of the amount of bleeding at the surgical site, command the voltage generator to cease providing the ablation energy at the ablation frequency and to provide a coagulation energy at a coagulation frequency, or, in response to a determination, from the sensing energy, of the amount of saline at the surgical site, change a flow rate of the saline to or from the surgical site.

2. The electrosurgical controller of claim 1:

wherein, when the processor calculates the control impedance, the processor is further configured to calculate the control impedance indicative of the amount of bleeding at the surgical site.

3. The electrosurgical controller of claim 2 wherein the processor is further configured to:

command the voltage generator to cease providing the coagulation energy at the coagulation frequency based on the control impedance; and command the voltage generator to cease providing the coagulation energy at the ablation frequency; and command the voltage generator to again provide the ablation energy at the ablation frequency.

4. The electrosurgical controller of claim 1:
wherein, when the processor calculates the control impedance, the processor is further configured to calculate the control impedance indicative of the amount of saline at the surgical site; and
wherein the processor is further configured to control the amount of saline at the surgical site based on the control impedance indicative of saline.

5. The electrosurgical controller of claim 1 wherein the ablation energy at the ablation frequency is selected to create a plasma within the surgical site.

6. The electrosurgical controller of claim 1 wherein the processor is further configured to:
calculate an ablative impedance experienced by the ablation energy at the ablation frequency; and
command the voltage generator to modify the ablation energy based on the ablative impedance.

7. The electrosurgical controller of claim 1 wherein the voltage generator further comprises:
an ablation generator defining an ablation output coupled to the active terminal, the ablation generator configured to produce the ablation energy at the ablation frequency; and
a sensing generator defining a sensing output coupled to the active terminal, the sensing generator configured to produce the sensing energy at the sensing frequency.

8. A system comprising:
an electrosurgical wand defining an active electrode;
an electrosurgical controller comprising:
a voltage generator coupled to the active electrode, the voltage generator configured to create and supply to the active electrode a combined energy comprising an ablation energy at an ablation frequency and a sensing energy at a sensing frequency, the sensing energy supplied at a same time as the ablation energy, the ablation frequency different than the sensing frequency, and the voltage generator configured to apply the combined energy including both the ablation energy and the sensing energy to the active electrode of the electrosurgical wand;
a sensing circuit coupled to the voltage generator, the sensing circuit configured to sense, from the combined energy comprising both the ablation energy and the sensing energy, (i) a first current associated with the ablation frequency and (ii) a second current associated with the sensing frequency; and
a processor coupled to the voltage generator and the sensing circuit, the processor configured to:
select the sensing frequency based on which electrosurgical parameter of interest is to be measured, wherein the electrosurgical parameter of interest is an amount of bleeding at a surgical site, an amount of saline at a surgical site, a proximity of tissue to the active electrode, or a proximity of bone to the active electrode, wherein the sensing frequency is different for each of the respective electrosurgical parameters except for the amount of bleeding at the surgical site and the amount of saline at the surgical site;
calculate a control impedance experienced by the sensing energy at the sensing frequency based on the first current;
command the voltage generator to change a parameter of the ablation energy at the ablation frequency based on the control impedance; and
in response to a determination, from the sensing energy, of the amount of bleeding at the surgical site, command the voltage generator to cease providing the ablation energy at the ablation frequency and to provide a coagulation energy at a coagulation frequency, or, in response to a determination, from the sensing energy, of the amount of saline at the surgical site, change a flow rate of the saline to or from the surgical site.

9. The system of claim 8:
wherein when the processor calculates the control impedance, the processor is further configured to calculate the control impedance indicative of the amount of bleeding at the surgical site.

10. The system of claim 9 wherein the processor is further configured to:
command the voltage generator to cease providing the coagulation energy at the coagulation frequency based on the control impedance; and
command the voltage generator to cease providing the coagulation energy at the ablation frequency; and
command the voltage generator to again provide the ablation energy at the ablation frequency.

11. The system of claim 8:
wherein, when the processor calculates the control impedance, the processor is further configured to calculate the control impedance indicative of the amount of saline at the surgical site; and
wherein the processor is further configured to control the amount of saline at the surgical site based on the control impedance indicative of saline.

12. The system of claim 8 wherein the ablation energy at the ablation frequency is selected to create a plasma within the surgical site.

13. The system of claim 8 wherein the processor is further configured to:
calculate an ablative impedance experienced by the ablation energy at the ablation frequency; and
command the voltage generator to modify the ablation energy based on the ablative impedance.

14. The system of claim 8 wherein the voltage generator further comprises:
an ablation generator defining an ablation output coupled to the active electrode, the ablation generator configured to produce the ablation energy at the ablation frequency; and
a sensing generator defining a sensing output coupled to the active electrode, the sensing generator configured to produce the sensing energy at the sensing frequency.

15. A method of operating an electrosurgical wand including an active terminal coupled to an active electrode of the electrosurgical wand and a return terminal, the method comprising:
creating and supplying to the active electrode a combined energy comprising an ablation energy at an ablation frequency and a sensing energy at a sensing frequency, the ablation frequency different than the sensing frequency, the sensing energy supplied at a same time as the ablation energy, wherein the combined energy including both the ablation energy and the sensing energy is applied to the active electrode of the electrosurgical wand;
at a sensing circuit, sensing, from the combined energy comprising both the ablation energy and the sensing energy, (i) a sense current associated with the sensing frequency and (ii) an ablation current associated with the ablation frequency;
selecting the sensing frequency based on which electrosurgical parameter of interest is to be measured, wherein the electrosurgical parameter of interest is an amount of bleeding at a surgical site, an amount of saline at a surgical site, a proximity of tissue to the active electrode, or a proximity of bone to the active electrode, wherein the sensing frequency is different for each of the respective electrosurgical parameters except for the amount of bleeding at the surgical site and the amount of saline at the surgical site;

calculating a control impedance experienced by the sensing energy at the sensing frequency based on the sense current;

commanding the voltage generator to change a parameter of the ablation energy at the ablation frequency based on the control impedance; and in response to a determination, from the sensing energy, of the amount of bleeding at the surgical site, commanding the voltage generator to cease providing the ablation energy at the ablation frequency and to provide a coagulation energy at a coagulation frequency, or in response to a determination, from the sensing energy, of the amount of saline at the surgical site, changing a flow rate of the saline to or from the surgical site.

16. The method of claim 15, further comprising, when calculating the control impedance, calculating the control impedance indicative of the amount of bleeding at the surgical site.

17. The method of claim 16, further comprising:

ceasing providing the coagulation energy at the coagulation frequency based on the control impedance;

ceasing providing the coagulation energy at the ablation frequency; and again providing the ablation energy at the ablation frequency.

18. The method of claim 15 further comprising:

when calculating the control impedance, calculating the control impedance indicative of the amount of saline at the surgical site; and controlling the amount of saline at the surgical site based on the control impedance indicative of saline.

19. The method of claim 15, wherein the ablation energy at the ablation frequency is selected to create a plasma within the surgical site.

20. The method of claim 15, further comprising:

calculating an ablative impedance experienced by the ablation energy at the ablation frequency; and modifying the ablation energy based on the ablative impedance.

* * * * *